United States Patent [19]
Sharaf

[11] Patent Number: 5,873,052
[45] Date of Patent: Feb. 16, 1999

[54] ALIGNMENT-BASED SIMILARITY SCORING METHODS FOR QUANTIFYING THE DIFFERENCES BETWEEN RELATED BIOPOLYMER SEQUENCES

[75] Inventor: Muhammad A. Sharaf, Oakland, Calif.

[73] Assignee: The Perkin-Elmer Corporation, Foster City, Calif.

[21] Appl. No.: 744,490

[22] Filed: Nov. 6, 1996

[51] Int. Cl.⁶ .............................. G06F 19/00; G06F 17/00
[52] U.S. Cl. ........................ 702/20; 702/19; 364/528.01
[58] Field of Search ..................................... 364/496, 497, 364/498, 499, 578, 528.01, 528.03; 702/22, 19.2

[56] References Cited

U.S. PATENT DOCUMENTS

| | | | |
|---|---|---|---|
| 5,436,850 | 7/1995 | Eisenberg et al. | 364/496 |
| 5,632,041 | 5/1997 | Peterson et al. | 395/800 |
| 5,701,256 | 12/1997 | Marr et al. | 364/496 |

FOREIGN PATENT DOCUMENTS

| | | | |
|---|---|---|---|
| 0 646 883 | 9/1994 | European Pat. Off. | G06F 17/30 |
| 2283840 | 11/1994 | United Kingdom | G06F 19/00 |
| PCT/SE95/ 01213 | 5/1996 | WIPO . | |

OTHER PUBLICATIONS

DePetrillo et al., "Derivation of a Scale–Independent Paratmeter Which Characterizes Genetic Seuence Comparisons," Computer and Biomedical Research 25 :517–540 1993.

Mark S. Johnson A Structural Basis for Sequence Comparisons J. Mol Biol. vol. 233 II 716–738, 1993.

Leung et al. J. Mol. Biol., 221: 1367–1378 (1991), An Efficient Algorithm for Identifying Matches with Errors in Multiple Long Molecular Sequences.

Needleman et al. J. Mol. Biol., 48: 443–453, (1970), A General Method Applicable to the Search for Similarities in the Amino Acid Sequence of Two Proteins.

Gribskov et al., Proc. Natl. Acad. Sci., 84: 4355–4358 (1987), Profile analysis: Detection of distantly related proteins.

Karlin et al. Proc. Natl. Acad. Sci., 90: 5873–5877 (1993), Applications and statistics for multiple high–scoring segments in molecular sequences.

Pearson et al. Proc. Natl. Acad. Sci., 85: 2444–2448 (1988), Improved tools for biological sequence comparison.

Altschul et al. J. Mol. Biol., 215: 403–410, (1990), Basic Local Alignment Search Tool.

Altschul et al. Nature Genetics, 6:119–129, (1994), Issues in searching molecular sequence databases.

Altschul J. Mol. Biol., 219: 555–565, (1991), Amino Acid Substitution Matrices from an Information Theoretic Perspective.

Altschul J. Mol. Evol., 36:290–300, (1993), A Protein Alignment Scoring System Sensitive at all Evolutionary Distances.

Brutlag et al. Computers Chem., 17(2):203–207, (1993), BLAZE an implementation of the Smith–Waterman Sequence Comparison Algorithm on a massively parallel computer.

PE/Applied Biosystems Division Fax on Demand Catalog, Product Insert for Sequence Navigator™, Document ID #267502 (Aug. 2, 1996), Sequence Navigator™ for Automated DNA and Protein Sequence Comparisons.

Primary Examiner—Lila Feisee
Assistant Examiner—Nirmal S. Basi
Attorney, Agent, or Firm—Paul D. Grossman

[57] ABSTRACT

Methods for assigning a quantitative score to the relatedness of aligned polymorphic biopolymer sequences such that small differences between otherwise identical sequences are highlighted are disclosed, including computer systems and program storage devices for carrying out the methods on a computer. Specifically, the methods of the invention comprise the steps of providing a test sequence and a basis set of sequences such that the test sequence and the basis set of sequences are aligned; determining the identity of a monomer unit at a position m in the test sequence; assigning a value of 1 to a local matching probability $x_m$ if the monomer unit at position m in the test sequence matches any members of the basis set at position m, or, assigning a value of between 0 and 1 to a local matching probability $x_m$ if the monomer unit at position m in the test sequence does not match any members of the basis set at position m. In a preferred embodiment, the above method is performed at a plurality of sequence locations and the local matching probabilities are multiplied together to provide a global matching probability.

14 Claims, 6 Drawing Sheets

Basis Set

```
        m=7 m=9                                    m=26
GAGATG A R W A    TGTGCCTTCG    GGAAC Y GTGA
GAGATG A A W A    KGTGCCTTCG    GGAAC Y GTGA
GAGATG A R W A    KGTGCCTTCG    GGAAC Y GTGA
GAGATG A A W A    DGTGCCTTCG    GGAAC Y GTGA
GAGATG A A W A    KGTGCCTTCG    GGAAC Y GTGA
```

Test Sequence

```
GAGATG G A T T    GGTGCCTTCG    GGAAC T GTGA
```

Fig. 5

|   |   | 110 | | 120 | | 130 | | 140 | | 150 | | 160 | | 170 |
|---|---|---|---|---|---|---|---|---|---|---|---|---|---|---|
|   |   | ↓ | ↓ | ↓ | | | | ↓ | | ↓ | | | | |
| 1 | LIB_SEC_16S0776F.1 | AGGTTRAAAC | TCARATGAAT | KGACGGGGGC | CCGCACAAGC | GGTGGAGCAT | KGACGGGGGC... wait |
| 1 | LIB_SEC_16S0776F.1 | AGGTTRAAAC | TCARATGAAT | KGACGGGGGC | CCGCACAAGC | GGTGGAGCAT | GTGGTTTAAT | TCGATGCAAC |
| 2 | LIB_SEC_16S0776F.2 | AGGTTAAAAC | TCAAATGAAT | TGACGGGGGC | CCGCACAAGC | GGTGGAGCAT | GTGGTTTAAT | TCGATGCAAC |
| 3 | LIB_SEC_16S0776F.3 | AGGTTAAAAC | TCAAATGAAT | TGACGGGGGC | CCGCACWAGC | GGTGGAGCAT | GTGGTTTAAT | TCGATGCAAC |
| 4 | LIB_SEC_16S0776F.4 | AGGTTAAAAC | TCAAATGAAT | TGACGGGGGC | CCGCACAAGC | GGTGGAGCAT | GTGGTTTAAT | TCGATGCAAC |
| 5 | •TEST PE35 0157 | <== | | | | | | |
| 6 | LIB_ PE29 0157 | AGGTTAAAAC | TCAAATGAAT | TGACGGGGGC | CCGCACAAGC | GGTGGAGCAT | GTGGTTTAAT | TCGATGCAAC |
| 7 | LIB_ PE30 0157 | AGGTTAAAAC | TCAAATGAAT | TGACGGGGGC | CCGCACAAGC | GGTGGAGCAT | GTGGTTTAAT | TCGATGCAAC |
| 8 | LIB_ PE56 0157 | AGGTTAAAAC | TCAAATGAAT | TGACGGGGGC | CCGCACAAGC | GGTGGAGCAT | GTGGTTTAAT | TCGATGCAAC |
| 11 |   | –––*–––––– | –––*–––––– | *––––––––– | –––––*–––– | –––––––––– | –––––––––– | –––––––––– |

|   |   | 180 | | 190 | | 200 | | 210 | | 220 | | 230 | | 240 |
|---|---|---|---|---|---|---|---|---|---|---|---|---|---|---|
|   |   | | | ↓ | | | | ↓↓↓ | | ↓↓↓ | | | | ↓ |
| 1 | LIB_SEC_16S0776F.1 | GCGAAGAACC | TTACCTGGTC | TTWGACATCCA | CGGAASTTTC | CAGAGATGAA | WADGTGCCTT | CGGGAACTGT |
| 2 | LIB_SEC_16S0776F.2 | GCGAAGAACC | TTACCTGGTC | TTGACATCCA | CRGAASTTTC | CAGAGATGAA | WATGTGCCTT | CGGGAACTGT |
| 3 | LIB_SEC_16S0776F.3 | GCGAAGAACC | TTACCTGGTC | TTGACATCCA | CRGAAGTTTC | CAGAGATGAA | WAKGTGCCTT | CGGGAACTGT |
| 4 | LIB_SEC_16S0776F.4 | GCGAAGAACC | TTACCTGGTC | TTGACATCCA | CAGAACTTTC | CAGAGATGAA | WAKGTGCCTT | CGGGAACTGT |
| 5 | •TEST PE35 0157 | <== | | | | | | |
| 6 | LIB_ PE29 0157 | GCGAAGAACC | TTACCTGGTC | TTGACATCCA | CAGAACTTTC | CAGAGATGGA | TTGGTGCCTT | CGGGAACTGT |
| 7 | LIB_ PE30 0157 | GCGAAGAACC | TTACCTGGTC | TTGACATCCA | CAGAACTTTC | CAGAGATGGA | TTGGTGCCTT | CGGGAACTGT |
| 8 | LIB_ PE56 0157 | GCGAAGAACC | TTACCTGGTC | TTGACATCCA | CAGAACTTTC | CAGAGATGGA | TTGGTGCCTT | CGGGAACTGT |
| 11 |   | –––––––––– | –––––*–––– | –––*–––––– | –––*–*–––– | ––––––––*– | ***––––––– | –––––––––– |

Fig. 6

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (v i) ORIGINAL SOURCE: Basis Set (Fig. 5)

(x i) SEQUENCE DESCRIPTION: SEQ ID NO:1:

GAGATGARWA TGTGCCTTCG GGAACYGTGA 30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i) ORIGINAL SOURCE: Basis Set (Fig. 5)

(x i) SEQUENCE DESCRIPTION: SEQ ID NO:2:

GAGATGAAWA KGTGCCTTCG GGAACYGTGA 30

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i) ORIGINAL SOURCE: Basis Set (Fig. 5)

(x i) SEQUENCE DESCRIPTION: SEQ ID NO:3:

GAGATGARWA KGTGCCTTCG GGAACYGTGA 30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i) ORIGINAL SOURCE: Basis Set (Fig. 5)

(x i) SEQUENCE DESCRIPTION: SEQ ID NO:4:

GAGATGAAWA DGTGCCTTCG GGAACYGTGA 30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i) ORIGINAL SOURCE: Basis Set (Fig. 5)

(x i) SEQUENCE DESCRIPTION: SEQ ID NO:5:

GAGATGAAWA KGTGCCTTCG GGAACYGTGA 30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i) ORIGINAL SOURCE: Test Sequence (Fig. 5)

(x i) SEQUENCE DESCRIPTION: SEQ ID NO:6:

GAGATGGATT GGTGCCTTCG GGAACTGTGA                                                        30

( 2 ) INFORMATION FOR SEQ ID NO:7:

( i ) SEQUENCE CHARACTERISTICS:
          ( A ) LENGTH: 140 base pairs
          ( B ) TYPE: nucleic acid
          ( C ) STRANDEDNESS: single
          ( D ) TOPOLOGY: linear ( v i ) ORIGINAL SOURCE: LIB_SEC_16S0776F.1 (Fig. 6)

( x i ) SEQUENCE DESCRIPTION: SEQ ID NO:7:

AGGTTRAAAC TCARATGAAT KGACGGGGGC CCGCACAAGC GGTGGAGCAT GTGGTTTAAT              60

TCGATGCAAC GCGAAGAACC TTACCTGGTC TWGACATCCA CGGAASTYTC CAGAGATGAA           120

WADGTGCCTT CGGGAACYGT                                                                      140

( 2 ) INFORMATION FOR SEQ ID NO:8:

( i ) SEQUENCE CHARACTERISTICS:
          ( A ) LENGTH: 140 base pairs
          ( B ) TYPE: nucleic acid
          ( C ) STRANDEDNESS: single
          ( D ) TOPOLOGY: linear ( v i ) ORIGINAL SOURCE: LIB_SEC_16S0776F.2 (Fig. 6)

( x i ) SEQUENCE DESCRIPTION: SEQ ID NO:8:

AGGTTAAAAC TCAAATGAAT TGACGGGGGC CCGCACAAGC GGTGGAGCAT GTGGTTTAAT              60

TCGATGCAAC GCGAAGAACC TTACCTGGTC TTGACATCCA CRGAAGTTTC CAGAGATGAR           120

WATGTGCCTT CGGGAACYGT                                                                      140

( 2 ) INFORMATION FOR SEQ ID NO:9:

( i ) SEQUENCE CHARACTERISTICS:
          ( A ) LENGTH: 140 base pairs
          ( B ) TYPE: nucleic acid
          ( C ) STRANDEDNESS: single
          ( D ) TOPOLOGY: linear ( v i ) ORIGINAL SOURCE: LIB_SEC_16S0776F.3 (Fig. 6)

( x i ) SEQUENCE DESCRIPTION: SEQ ID NO:9:

AGGTTAAAAC TCAAATGAAT TGACGGGGGC CCGCACWAGC GGTGGAGCWT GTGGTTTAAT              60

TCGATGCAAC GCGAAGAACC TTACCTGGTC TTGACATCCA CRGAASTTTC CAGAGATGAA           120

WAKGTGCCTT CGGGAACYGT                                                                      140

( 2 ) INFORMATION FOR SEQ ID NO:10:

( i ) SEQUENCE CHARACTERISTICS:
          ( A ) LENGTH: 140 base pairs
          ( B ) TYPE: nucleic acid
          ( C ) STRANDEDNESS: single
          ( D ) TOPOLOGY: linear ( v i ) ORIGINAL SOURCE: LIB_SEC_16S0776F.4 (Fig. 6)

( x i ) SEQUENCE DESCRIPTION: SEQ ID NO:10:

AGGTTAAAAC TCAAATGAAT TGACGGGGGC CCGCACAAGC GGTGGAGCAT GTGGTTTAAT              60

TCGATGCAAC GCGAAGAACC TTACCTGGTC TTGACATCCA CRGAAGTTTC CAGAGATGAR           120

WAKGTGCCTT CGGGAACYGT                                                                      140

( 2 ) INFORMATION FOR SEQ ID NO:11:

(i) SEQUENCE CHARACTERISTICS:
    (A) LENGTH: 140 base pairs
    (B) TYPE: nucleic acid
    (C) STRANDEDNESS: single
    (D) TOPOLOGY: linear (vi) ORIGINAL SOURCE: TEST PE35 0157 (Fig. 6)

(xi) SEQUENCE DESCRIPTION: SEQ ID NO:11:

| AGGTTAAAAC | TCAAATGAAT | TGACGGGGGC | CCGCACAAGC | GGTGGAGCAT | GTGGTTTAAT | 60 |
| TCGATGCAAC | GCGAAGAACC | TTACCTGGTC | TTGACATCCA | CAGAACTTTC | CAGAGATGGA | 120 |
| TTGGTGCCTT | CGGGAACTGT | | | | | 140 |

(2) INFORMATION FOR SEQ ID NO:12:

(i) SEQUENCE CHARACTERISTICS:
    (A) LENGTH: 140 base pairs
    (B) TYPE: nucleic acid
    (C) STRANDEDNESS: single
    (D) TOPOLOGY: linear (vi) ORIGINAL SOURCE: TEST PE29 0157 (Fig. 6)

(xi) SEQUENCE DESCRIPTION: SEQ ID NO:12:

| AGGTTAAAAC | TCAAATGAAT | TGACGGGGGC | CCGCACAAGC | GGTGGAGCAT | GTGGTTTAAT | 60 |
| TCGATGCAAC | GCGAAGAACC | TTACCTGGTC | TTGACATCCA | CAGAACTTTC | CAGAGATGGA | 120 |
| TTGGTGCCTT | CGGGAACTGT | | | | | 140 |

(2) INFORMATION FOR SEQ ID NO:13:

(i) SEQUENCE CHARACTERISTICS:
    (A) LENGTH: 140 base pairs
    (B) TYPE: nucleic acid
    (C) STRANDEDNESS: single
    (D) TOPOLOGY: linear (vi) ORIGINAL SOURCE: TEST PE30 0157 (Fig. 6)

(xi) SEQUENCE DESCRIPTION: SEQ ID NO:13:

| AGGTTAAAAC | TCAAATGAAT | TGACGGGGGC | CCGCACAAGC | GGTGGAGCAT | GTGGTTTAAT | 60 |
| TCGATGCAAC | GCGAAGAACC | TTACCTGGTC | TTGACATCCA | CAGAACTTTC | CAGAGATGGA | 120 |
| TTGGTGCCTT | CGGGAACTGT | | | | | 140 |

(2) INFORMATION FOR SEQ ID NO:14:

(i) SEQUENCE CHARACTERISTICS:
    (A) LENGTH: 140 base pairs
    (B) TYPE: nucleic acid
    (C) STRANDEDNESS: single
    (D) TOPOLOGY: linear (vi) ORIGINAL SOURCE: TEST PE56 0157 (Fig. 6)

(xi) SEQUENCE DESCRIPTION: SEQ ID NO:14:

| AGGTTAAAAC | TCAAATGAAT | TGACGGGGGC | CCGCACAAGC | GGTGGAGCAT | GTGGTTTAAT | 60 |
| TCGATGCAAC | GCGAAGAACC | TTACCTGGTC | TTGACATCCA | CAGAACTTTC | CAGAGATGGA | 120 |
| TTGGTGCCTT | CGGGAACTGT | | | | | 140 |

ALIGNMENT-BASED SIMILARITY SCORING METHODS FOR QUANTIFYING THE DIFFERENCES BETWEEN RELATED BIOPOLYMER SEQUENCES

FIELD OF THE INVENTION

This invention relates to methods for quantitatively determining the relatedness of biopolymer sequences. More specifically, the invention is directed to methods for scoring aligned polymorphic biopolymer sequences such that small differences between otherwise identical sequences are highlighted, including computer systems and program storage devices for carrying out such methods using a computer.

REFERENCES

Altschul, et al., *J Mol. Biol.*, 215: 403–410 (1990)

Brutlag, et al., *Comput. Chem.* 17: 203–207 (1993)

Gribskov, et al., *Proc. Natl. Acad. Sci.* USA, 84: 4355–4358 (1987)

Higgins et al., *Comput. Applic. Biosci.*, 8, 189–191 (1992)

Needleman and Wunsch, *Mol. Biol.*, 48: 443–453 (1970)

Nomenclature Committee of the International Union of Biochemistry (NC-IUB), *Eur. J Biochem.*, 150:1 (1985)

Pearson and Lipman, *Proc. Natl. Acad. Sci.* USA, 85: 2444–2448 (1988)

BACKGROUND

The identification of sequence homology between an unknown biopolymer test sample and a known gene or protein often provides the first clues about the function and/or the three dimensional structure of a protein, or the evolutionary relatedness of genes or proteins. Because of the recent explosion in the amount of DNA sequence information available in public and private databases as a result of the human genome project and other large scale DNA sequencing efforts, the ability to screen newly discovered DNA sequences against databases of known genes and proteins has become a particularly important aspect of modern biology.

Generally, the sequence comparison problem may be divided into two parts: (1) alignment of the sequences and (2) scoring the aligned sequences. Alignment refers to the process of introducing "phase shifts" and "gaps" into one or both of the sequences being compared in order to maximize the similarity between two sequences, and scoring refers to the process of quantitatively expressing the relatedness of the aligned sequences.

Existing sequence comparison processes may be divided into two main classes: global comparison methods and local comparison methods. In global comparison methods, the entire pair of sequences are aligned and scored in a single operation (Needlman and Wunsch), and in local comparison methods, only highly similar segments of the two sequences are aligned and scored and a composite score is computed by combining the individual segment scores, e.g., the FASTA method (Pearson and Lipman), the BLAST method (Altschul) and the BLAZE method (Brutlag).

Application of existing alignment-based similarity scoring methods is problematic in applications where a high degree of sensitivity is required, i.e., where very similar sequences are being compared, e.g., two 1500-base 16S rDNA sequences differing by only 1–5 bases. An alignment-based similarity score, especially one based on local alignments such as FASTA (Pearson and Lipman) or BLAST (Altschul), will tend to emphasize the similarity of sequences and overlook small differences between them. In applications where small differences are critical, e.g., distinguishing the 16S RNA sequences of *E. Coli* K-12 (benign) and *E. Coli* O157 H:7 (pathogenic), it is crucial to be able to detect small differences between sequences rather than similarities.

An additional shortcoming of existing similarity scoring methods is that they fail to take into account the polymorphic nature of the sequences being compared, i.e., the fact that more than one monomer unit may be present in a given sequence at a given position, and that the proportion of each monomer at that position may be variable such that a minor component may go undetected. Such polymorphisms can arise when the sequencing template is a polymorphic multicopy gene which has been amplified by the PCR. For example, consider a set of sequences which are polymorphic at a position m, e.g., sequences derived from a sample including 10 copies of a polymorphic gene. Furthermore, assume that the polymorphism is such that in 8 of the copies of the gene the nucleotide at position m is an A and in the remaining two copies of the gene the nucleotide is a C. Thus, in an ideal sequencing experiment, each of the members of the set would show a signal having an 80% A component and a 20% C component at position m. However, in reality, many automated sequencing methods do not have the capability to reliably detect the presence of a 20% minor component. In such a case, the basis set would show only an A nucleotide at position m while the true situation would be that 20% of the polymorphic genes have a C at that position. Using existing similarity scoring methods, position m would be deemed to be a non-match, i.e., existing methods would erroneously conclude that a test sequence that included a C at position m was not a member of the set of known sequences.

Thus, what is needed is an alignment-based similarity scoring method (i) capable of quantitatively distinguishing very similar sequences and (ii) capable of taking into account the polymorphic nature of many biopolymer sequences in light of the inability of current sequencing technology to reliably detect a polymorphic nucleotide present as a minor component.

SUMMARY

The present invention is directed towards an alignment-based similarity scoring method for quantifying differences between closely related polymorphic biopolymer sequences, e.g., DNA, RNA, or protein sequences.

It is an object of the invention to provide an alignment-based similarity scoring method which is capable of meaningfully distinguishing sequences having a sequence homology of greater than 99%.

It is another object of the invention to provide an alignment-based similarity scoring method which is capable of distinguishing polymorphic sequences in a statistically meaningful way.

In a first aspect, the foregoing and other objects of the invention are achieved by a method comprising the steps of providing a test sequence and a basis set of sequences where the test sequence and the basis set of sequences are aligned; determining the identity of a monomer unit at a position m in the test sequence; and assigning a value of 1 to a local matching probability $x_m$ if the monomer unit at position m in the test sequence matches any members of the basis set at position m, or, assigning a value of between 0 and 1 to a local matching probability $x_m$ if the monomer unit at position m in the test sequence does not match any members of the basis set at position m. Preferably, if the monomer unit at position m in the test sequence does not match any members of the basis set at position m, $x_m$ is assigned a value of $$x_m = (1-p)^n$$

where p is a number between 0 and 1 and n is the number of sequences in the basis set at position m. Preferably, p is between 0.4 and 0.6, and more preferably p is 0.5. In a second preferred embodiment, the step of determining the identity of a monomer unit at a position m in the test sequence and the step of assigning a value to the local matching probability $x_m$ are performed at a plurality of positions m in the test sequence such that a plurality of local matching probabilities $x_m$ are determined; and a global matching probability for the basis set and the test sequence is computed, $X_G$, by forming a product of the plurality of $x_m$. Preferably, the local matching probabilities are determined for each position m in the test sequence and the global matching probability for the basis set and the test sequence is determined by computing the product $$X_G = \prod_{1}^{M} x_m.$$

In yet another preferred embodiment, the above-described method is performed on each of a plurality of test sequences, and a statistical measure of a combined value of the local or global matching probabilities is determined, e.g., an average value, a standard deviation, a maximum value, or a minimum value.

In a further preferred embodiment of the method of the invention, the above-described method is performed using a plurality of values of p and an optimum value of $X_G$ is determined.

In a second aspect, the invention comprises a program storage device readable by a machine, tangibly embodying a program of instructions executable by a machine to perform the above-described method steps to quantify differences between closely related aligned biopolymer sequences.

In a third aspect, the invention includes a computer system for determining a similarity score for a test sequence and a basis set of sequences comprising an input device for inputting a test sequence and a basis set of sequences such that the test sequence and the basis set of sequences are aligned; a memory for storing the test sequence and basis set; a processing unit configured for determining the identity of a monomer unit at a position m in the test sequence; and assigning a value of 1 to a local matching probability $x_m$ if the monomer unit at position m in the test sequence matches any members of the basis set at position m, or, assigning a value of between 0 and 1 to a local matching probability $x_m$ if the monomer unit at position m in the test sequence does not match any members of the basis set at position m.

These and other objects, features, and advantages of the present invention will become better understood with reference to the following description, drawings, and appended claims.

BRIEF DESCRIPTION OF THE DRAWINGS

FIG. 5 shows an alignment of an exemplary basis set and test sequence.

FIG. 6 shows the two basis sets and a test sequence to be compared by both the method of the present invention and the FASTA method.

DETAILED DESCRIPTION OF THE PREFERRED EMBODIMENTS

Figure 1:
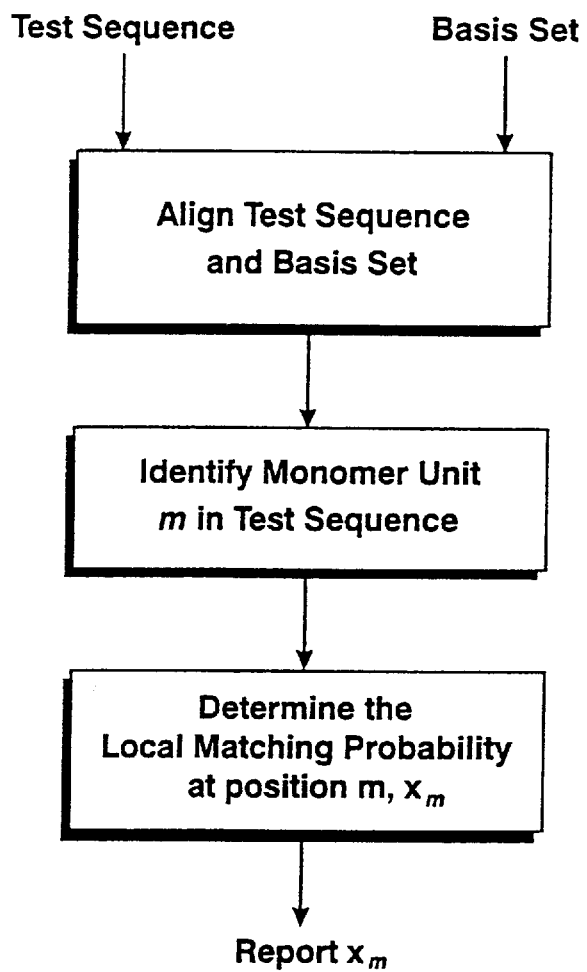
FIGS. 1, 2, and 3 are flow charts depicting various preferred similarity scoring methods of the invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims. For the sake of clarity, the method and apparatus will be described primarily with respect to polynucleotide sequences, however it will be apparent to one of ordinary skill in the art that the concepts discussed are applicable to any experimentally derived collection of biopolymer sequences.

I. DEFINITIONS

Unless stated otherwise, the following terms and phrases as used herein are intended to have the following meanings:

The term "monomer unit" refers to an individual unit making up a biopolymer sequence, e.g., a particular amino acid in a protein or a particular nucleotide in a polynucleotide. In the case of a polynucleotide sequence, the monomer may be a combination of nucleotides, nomenclature of such combinations being defined by the IUB code as follows (Nomenclature Committee)

R=G and A
Y=T and C
W=A and T
S=G and C
M=A and C
K=G and T
B=G and T and C
D=G and A and T
V=G and A and C
H=A and T and C
N=G and A and T and C The term "polymorphism" refers to a location in a sequence at which more than one monomer unit resides, e.g., an A nucleotide and a G nucleotide. Such polymorphisms may arise when the sequencing template is made up of multiple polynucleotides having different nucleotides at a particular position.

The term "test sequence" refers to a biopolymer sequence to be compared to a basis set of biopolymer sequences.

The term "basis set" refers to a collection of biopolymer sequences to be compared to a test sequence.

The term "minor component" refers to a monomer unit at a polymorphic position which has the smaller of any two signals at that position. The term "major component" refers to a monomer unit at a polymorphic position which has the larger of any two signals at that position.

A "match" occurs when a monomer unit at a position m in a test sequence is present at the position m of any one of the members of a basis set of sequences. In the case of polynucleotide sequences, either one of two types of matches may be employed in the methods of the invention depending upon how monomer units represented by IUB codes are treated. In a first type of match, referred to as an "exact match", the monomer unit of the test sequence and the members of the basis set must match exactly, including monomer units represented by IUB codes. Thus, if a test sequence contained a "W" (A and T) at position m, a basis set containing only a T at that position would not be considered a match. Alternatively, in a second type of match, referred to as an "TUB match", a match with either of the members of the IUB pair would be scored as a match. Thus, if a test sequence contained a "W" (A and T) at position m, a basis set containing only a T at that position would be considered a match. Either type of match may be applied to the methods of the present invention.

II. SCORING METHOD

The similarity scoring method of the present invention is directed to a method for scoring aligned biopolymer sequences such that small differences between otherwise identical sequences are highlighted and such that the polymorphic character of the sequences is accounted for in a quantitative, statistically meaningful way. Generally, the method of the invention includes the following steps. A test sequence and a basis set of sequences are provided wherein the test sequence and the basis set of sequences are aligned. The identity of a monomer unit at a position m in the test sequence is determined. A local matching probability xm is determined where a value of 1 is assigned to the local matching probability if the monomer unit at position m in the test sequence matches any of the members of the basis set at position m. Alternatively, a value of between 0 and 1 is assigned to the local matching probability $x_m$ if the monomer unit at position m in the test sequence does not match any of the members of the basis set at position m.

A. Test Sequence and Basis Set of Sequences

A1. Test Sequence

A test sequence according to the similarity scoring method of the invention may be any biopolymer sequence of interest, e.g., protein, nucleic acid, PNA, and the like. Preferably, the test sequence is a protein or nucleic acid sequence. More preferably, the test sequence is a nucleic acid sequence. According to the nomenclature used herein, the test sequence is described as an M-element linear array of monomer units located at positions m equal to 1 through M.

The test sequence may be derived from any biological organism or remains thereof For example, the test sequence may be a gene coding for a 16S RNA molecule of a medically important microorganism. In one preferred alternative, the test sequence is a consensus sequence derived from a collection of biopolymer sequences. In an alternative preferred embodiment, the test sequence is derived from an assembly of partially overlapping sequences.

A2. Basis Set of Sequences

A basis set according to the invention comprises a set of biopolymer sequences derived from a plurality of related basis templates located in a biological sample. The basis set may be composed of sequences which are derived from homomorphic polynucleotide templates, e.g., templates derived from a single copy cloned gene. In such a case, any polymorphism seen in the sequence of a member of the basis set is due only to an erroneous base call caused by the inherent variability of the sequencing process, e.g., variability due to enzymatic misincorporation of dideoxynucleotide triphosphate terminators, incomplete resolution of neighboring species in a sequencing gel resulting in signal overlap, finite detection limits of labels, uncertainties associated with the particular base-calling algorithm used, contamination of samples, and the like.

Alternatively, the basis set may be composed of sequences which are derived from polymorphic polynucleotide templates, e.g., templates derived from PCR amplification of a multicopy gene wherein the multiple copies have different sequences. Here, the variability among members of the basis set is due to both the inherent variability of the sequencing process and the true sequence differences among the templates used to derive the basis set.

The basis set can be conveniently described as an N×M matrix where N is the total number of sequences in the basis set and M is the number of monomer units making up the test sequence.

B. Alignment of Test Sequence and Basis Set

As described in the Background section of this disclosure, alignment refers to the process of introducing "phase shifts" and "gaps" into sequences being compared in order to maximize the similarity between the two sequences. Any method for sequence alignment may be used with the similarity scoring methods of the present invention. Exemplary alignment methods include CLUSTAL (liggins) and Needleman-Wunsch (Needleman).

C. Scoring Relatedness of a Test Sequence and a Basis Set

C1. Scoring of Individual Monomer Units

To assign a quantitative similarity score to the relatedness of a monomer unit at a given location m in a test sequence and the set of monomer units at the same location m in a basis set of sequences, a value for a local matching probability $x_m$ is assigned to the position m, where the local matching probability is the probability that a monomer unit at a position m in the test sequence is a member of the set of monomer units at position m in the sequences making up the basis set, and $1-x_m$ is the probability that a monomer unit at position m in the test sequence is not a member of the set of monomer units at position m in the sequences making up the basis set. The method is generally described in the flow chart of FIG. 1.

In the similarity scoring method of the invention, if the monomer unit at position m in the test sequence matches any of the members of the basis set at position m, $x_m$ is assigned a value of 1. Thus for example, if the test sequence is

ACCGT and the basis set is

ACAGG
ACGGA
ACAGT the value of $x_5$ would be 1 because of the presence of a T at position 5 of the third member of the basis set.

Alternatively, if the monomer unit at position m in the test sequence does not match any of the members of the basis set at position m, the local matching probability $x_m$ is assigned a value of between 0 and 1. Conceptually, $x_m$ corresponds to a maximum probability that a monomer unit is in fact present at position m in at least one of the basis templates used to generate the basis set yet is not represented in the basis set itself because of the inability of the sequencing method used to generate the basis set to detect the monomer unit. Thus, even if the monomer unit is not represented at position m in any of the members of the basis set, the method of the invention assigns a finite probability that such monomer unit is in fact present in the population of basis templates used to generate the basis set, but is present at levels below that which the sequencing method employed to generate the basis set is able to detect.

A preferred method for determining the value of $x_m$ when the monomer unit at position m does not match the members of the basis set of N sequences is according to the relation $$x_m = (1-p)^n$$

where p is a number between 0 and 1 and n is the number of sequences in the basis set having an element at position m. Note that when the sequences of the basis set overlap at every position m, then n=N for each position m. However, when some members of the basis set do not overlap other members at certain positions, then n<N at those nonoverlapping positions m in the sequence.

Conceptually, the value of p is a measure of the sensitivity of the sequencing system used to generate the sequences making up the basis set, i.e., the ability of a sequencing system to detect minor components in a signal including both major and minor components. Sensitivity is determined by such factors as the detectability of the labels used to label the sequencing fragments, the ability of the analysis software to distinguish overlapping peaks in an electropherogram, and the like. A large value of p indicates that the sequencing system is highly sensitive while a small value of p indicates that the sequencing system has poor sensitivity and would miss all but the largest minor components. For example, consider a basis set composed of 5 sequences overlapping at position m, i.e., n=5. The value of $x_m$ for three different values of p when there are no matches between the basis set and the test sequence according to the relation provided above are $$p = 0.9 \quad x_m = 0.001\%$$
$$p = 0.5 \quad x_m = 3.1\%$$
$$p = 0.1 \quad x_m = 59.0\%.$$

Thus, when p=0.9, i.e., a sequencing system having good sensitivity, the calculated probability that a monomer unit at position m of the test sequence is not present in the basis set but is present as a minor component of the basis templates used to derive the basis set is very small, i.e., 0.001%. Conversely, when p=0.1, i.e., a sequencing system having poor sensitivity, the calculated probability that a monomer unit at position m of the test sequence does not match the basis set but is present as a minor component of the basis templates used to derive the basis set is significant, i.e., 59.0%.

A practical consequence of choosing a large or small value of p relates to the likelihood of false positive results vs. false negative results, a false negative result being a result indicating a test sequence is not a member of the basis set when in fact it is a member of the basis set, and a false positive result indicating a test sequence is a member of the basis set when in fact it is not a member of the basis set. If a large value of p is chosen, e.g., greater than 0.6, the likelihood of a false negative result is increased, while if a small value of p is chosen, e.g., less than 0.4, the likelihood of a false positive result is increased. Preferably, to balance the effects of false positive and false negative results, p is chosen to be from 0.4 and 0.6. More preferably, p is chosen to be approximately 0.5.

C2. Scoring of Multiple Monomer Units

Figure 2:
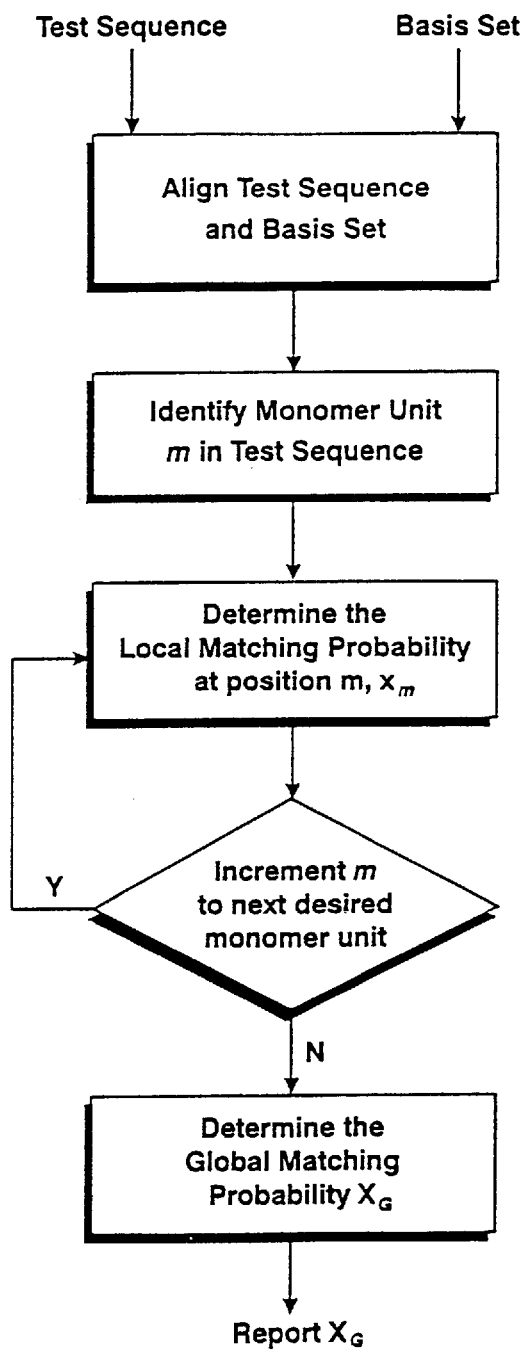

To assign a similarity score to the relatedness of a test sequence and a basis set of sequences based on a plurality of monomer units located at a plurality of positions m in the sequences, a value for the local matching probability $x_m$ is determined for each of a plurality of monomer units located at a plurality of positions m in the sequences. Then, a global matching probability $X_G$ is computed by forming the product of the individual matching probabilities. The method is generally described in the flow chart of FIG. 2. In a preferred embodiment, the value of $x_m$ is determined for each position of the test sequence and the product of all of the values of $x_m$ is computed according to the relation $$X_G = \prod_1^M x_m.$$

Figure 3:
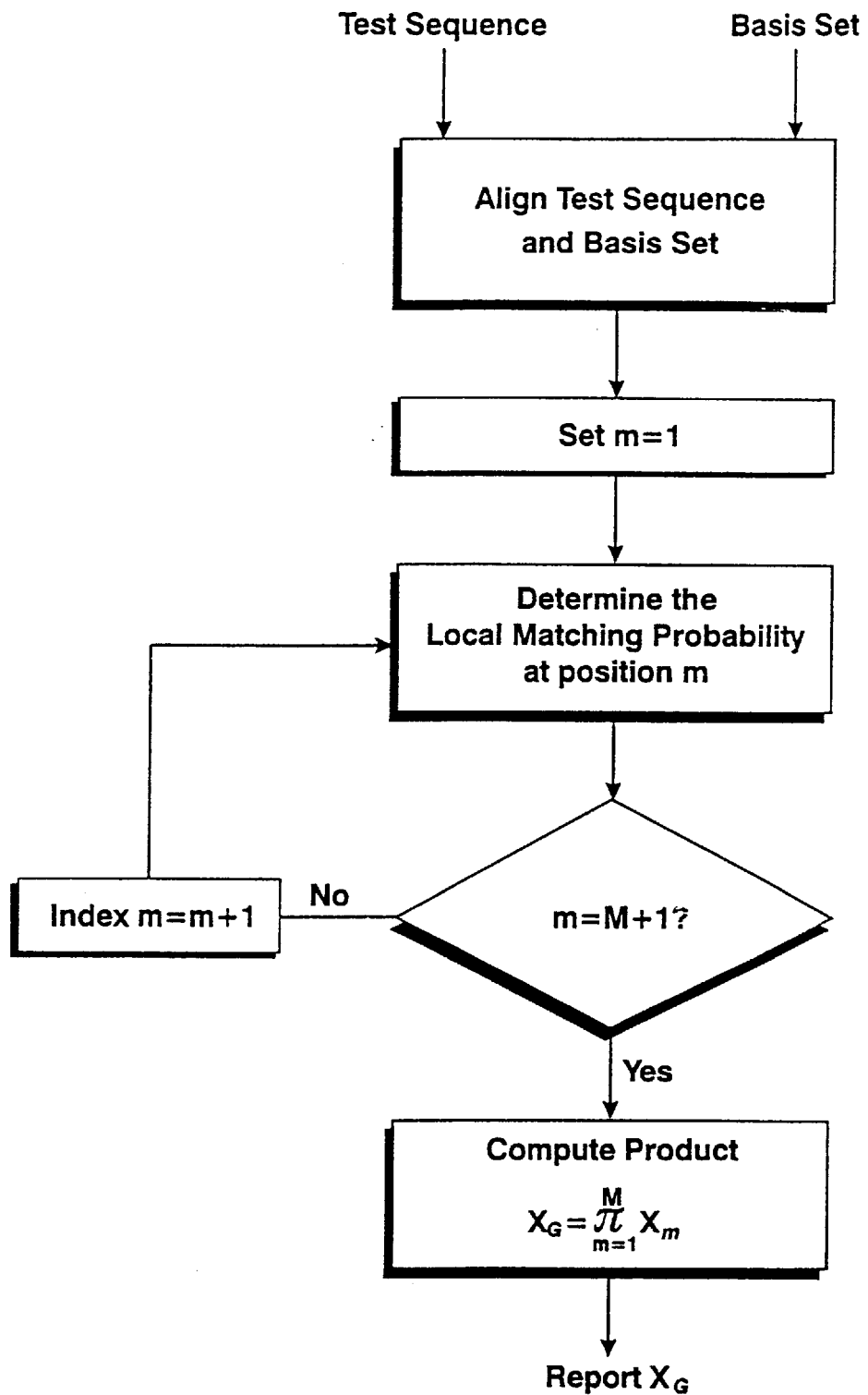

This preferred embodiment is generally described in the flow chart of FIG. 3

C3. Scoring Based on Multiple Test Sequences

In an alternative embodiment of the scoring method discussed above, rather than comparing a single test sequence with a basis set of sequences, a set of test sequences is compared with the basis set. In this embodiment, a local or global matching probability is determined for each member of the set of test sequences individually according to the methods described above. Then, any measure of the combined local or global matching probability for the set of test sequences may be determined, e.g., an average value of the matching probability including standard deviation, maximum values, minimum values, log $X_G$, or any other like statistical measures.

C4. Scoring Based on Variable Value of the Parameter p

In yet another alternative embodiment of the similarity scoring methods of the invention, rather than fixing the value of the parameter p at a constant value in the calculation of a matching probability, p is varied over a range of values. In this method, for a fixed value of p, a local or global matching probability is determined for an individual test sequence or set of test sequences as described above. Then, the value of p is changed, and the calculation of matching probabilities is repeated using the new value of p. This process is then repeated for a plurality of different values of p. Then, an optimum value or range of values of the matching probability is determined. This method using a variable value of p is particularly preferred when the test sequence is made up of a set of multiple test sequences as described in Section C3 above.

III. COMPUTER SYSTEM AND PROGRAM STORAGE DEVICE

Figure 4:
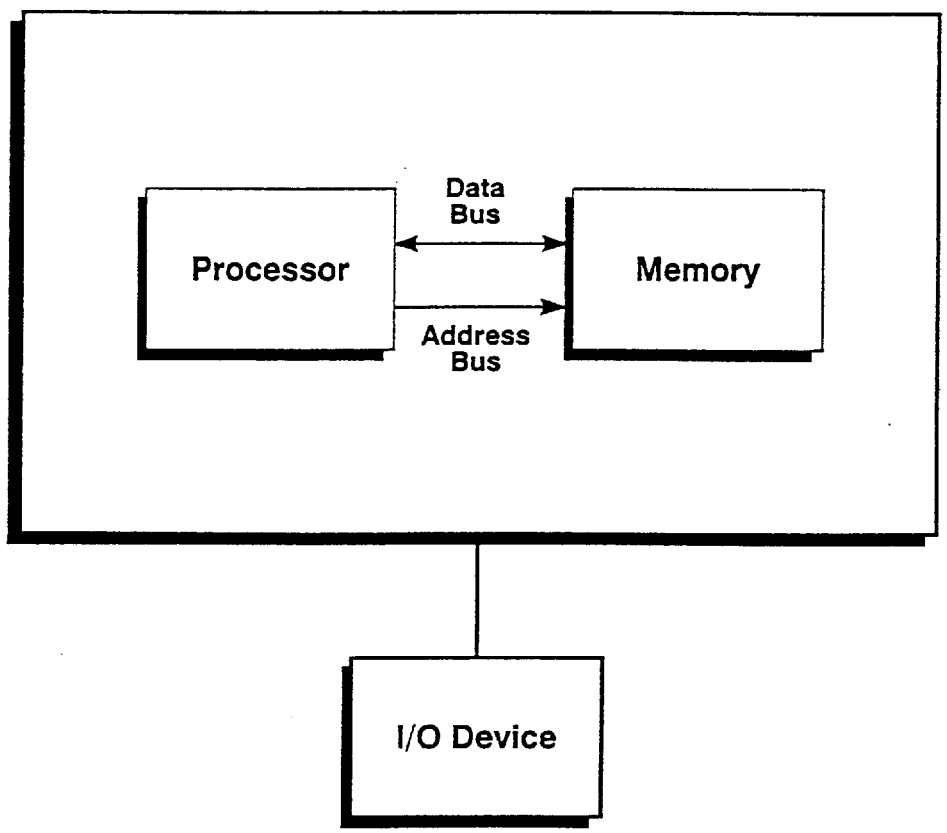
FIG. 4 is a schematic diagram of a preferred computer system of the invention.

The steps of above-describe scoring method are preferably performed by a computer. In one preferred embodiment, the computer is made up of a processing unit, memory, I/O device, and associated address/data bus structures for communicating information therebetween. See FIG. 4. The microprocessor can take the form of a generic microprocessor driven by appropriate software, including RISC and CISC processors, a dedicated microprocessor using embedded firmware, or a customized digital signal processing circuit (DSP) which is dedicated to the specific processing tasks of the method. The memory may be within the microprocessor, i.e., level 1 cache, fast S-RAM, i.e., level 2 cache, D-RAM, or disk, either optical or magnetic. The I/O device may be any device capable of transmitting information between the computer and the user, e.g., a keyboard, mouse, network card, and the like. The address/data bus may be PCI bus, NU bus, ISA, or any other like bus structure.

When the method is performed by a computer, the above-described method steps are embodied in a program storage device readable by a machine, such program storage device including a computer readable medium. Computer readable media include magnetic diskettes, magnetic tapes, optical disks, Read Only Memory, Direct Access Storage Devices, gate arrays, electrostatic memory, and any other like medium.

IV. EXAMPLES

The invention will be further clarified by a consideration of the following examples, which are intended to be purely exemplary of the invention and not to in any way limit its scope.

Example 1

Scoring the Similarity Between E. Coli Strain B and E. coli Strain O157 H:7

FIG. 5 shows an alignment of a basis set comprising multiple sequencing runs E. Coli Strain B (Sigma Chemical Co. p/n D4889) and a test sequence comprising a strain of E. Coli O157 H:7. The DNA sequences were obtained using the ABI PRISM™ Dye Terminator Cycle Sequencing Kit, AmpliTaq FS in combination with the ABI PRISM™ Model 377 DNA Sequencer according to manufacturers instructions (PE Applied Biosystems, Division of The Perkin-Elmer Corporation (PEABD), p/n 402080). The sequences were aligned using the Sequence Navigator™ software which employs the CLUSTAL multiple alignment method (PEABD p/n 401615).

As shown in FIG. 5, all 5 replicates of the Strain B basis set (see SEQ ID NO:1 through SEQ ID NO:5) show a base assignment of A at position m=7, while the O157 H:7 test sequence (SEQ ID NO:14 through SEQ ID NO:16) shows a G at that position.

The value of $x_m$ at position m=7 of the O157 H:7 test sequence was determined where p=0.5 and n=5 resulting in a value of $(0.5)^5=3.13\%$. The same procedure was applied at positions m=9 (W vs. T) and m=26 (Y vs. T). Based on only three base differences, it was inferred that the O157 H:7 test sequence is not a member of the basis set of Strain B sequences with a probability of greater than 99.99%, i.e., $(1-(3.13\%)^3)$.

Example 2

Comparison of the Method of the Invention with the FASTA Method for Scoring Related Sequences In this example, a similarity score was calculated for a test sequence and each of two basis sets of sequences using both the method of the invention and the FASTA method.

FIG. 6 shows the two basis sets and the test sequence used in this comparison. The first basis set, set 1, is composed of sequences 6–8 (SEQ ID NO:14 through SEQ ID NO:16) in the figure. These sequences were obtained from clinical isolates of E. coli strain O157. The second basis set, set 2, is composed of sequences 1–4 (SEQ ID NO:7 through SEQ ID NO:10) in the figure. These sequences were obtained from four replicate sequencing runs of E. coil strain B. The test sequence, sequence 5 (SEQ ID NO:11) in the figure, is a clinical isolate of E. coli strain O157. Thus, the test sequence is a member of set 1, in fact, the sequences are identical, but is not a member of set 2. The arrows at positions 106, 114, 121, 137, 149, 192, 208, and 220 in the figure indicate positions at which the sequences of set 2 are polymorphic with respect to each other. The arrows at positions 202, 206, 219, 221, 222, 223 and 238 in the figure indicate positions at which none of the sequences of set 2 match the test sequence. Note that in this experiment, only exact matches were counted as a match.

Scoring the similarity of the test sequence with set 1 and set 2 using the FASTA method as implemented in the GeneAssist™ software package (PEABD p/n 402233), using a k-tuple of 2, resulted in similarity scores of 1996 and 1942, respectively. Even though the test sequence is a member of set 1 and is not a member of set 2, the similarity scores only differed by approximately 2.5%. Thus, the FASTA method was not able to clearly distinguish which of the two basis sets the test sequence was a member of.

Scoring the similarity of the test sequence with set 1 and set 2 using the scoring method of the invention resulted in scores of essentially 100% and 0%, respectively, where p was set at 0.5 and n was set at 3 for comparison with set 1 and 4 for comparison with set 2. Thus, the scoring method of the invention clearly indicated the fact that the test sequence was a member of set 1, and that the test sequence was not a member of set 2, there being 7 mismatches between set 2 and the test sequence.

All publications and patent applications are herein incorporated by reference to the same extent as if each individual publication or patent application was specifically and individually indicated to be incorporated by reference.

Although only a few embodiments have been described in detail above, those having ordinary skill in the art will clearly understand that many modifications are possible in the preferred embodiment without departing from the teachings thereof. All such modifications are intended to be encompassed within the following claims.

---

We claim:

1. A processing method in a computer for determining a similarity score for a biopolymer test sequence and a basis set of sequences comprising the steps of:

(a) inputting a biopolymer test sequence and a basis set of biopolymer sequences such that the test sequence and the basis set of sequences are aligned;

(b) determining the identity of a monomer unit at a position m in the test sequence;

(c) outputting a value of 1 for a local matching probability $x_m$ if the monomer unit at position m in the test sequence matches any members of the basis set at position m, or, outputting a value of between 0 and 1 for a local matching probability $x_m$ if the monomer unit at position m in the test sequence does not match any members of the basis set at position m.

2. The method of claim 1 wherein if the monomer unit at position m in the test sequence does not match any members of the basis set at position m, outputting a value of $x_m$ $$x_m = (1-p)^n$$

where p is a number between 0 and 1 and n is the number of sequences in the basis set at position m.

3. The method of claim 1 wherein p is between 0.4 and 0.6.

4. The method of claim 1 wherein p is 0.5.

5. The method of claim 1 further comprising the steps of:
performing steps (b) and (c) at a plurality of positions m in the test sequence thereby determining a plurality of local matching probabilities $x_m$; and
determining a global matching probability for the basis set and the test sequence, $X_G$, by forming a product of the plurality of $x_m$.

6. The method of claim 5 wherein the global matching probability for the basis set and the test sequence, $X_G$, is determined by computing the product $$X_G = \prod_1^M x_m.$$

7. The method of claim 1 wherein the test sequence is a 16S RNA sequence from a microorganism, and the basis set comprises a plurality of 16S RNA sequences derived from a collection of microorganisms.

8. A processing method in a computer for determining a similarity score for a biopolymer test sequence and a basis set of sequences comprising the steps of:

(a) inputting a biopolymer test sequence and a basis set of biopolymer sequences wherein the test sequence and the basis set of sequences are aligned;

(b) determining the identity of a monomer unit at a position m in the test sequence;

(c) outputting a value of 1 for a local matching probability $x_m$ if the monomer unit at position m in the test sequence matches any members of the basis set at position m, or, outputting a value of $$x_m = (1-p)^n$$

for the local matching probability $x_m$ if the monomer unit at position m in the test sequence is not present in any members of the basis set at position m, where p is a number between 0 and 1 and n is the number of sequences in the basis set at position m;

(d) changing the value of p and repeating step (c); and (e) determining a range of values of p corresponding to the maximum value of $x_m$.

9. A program storage device readable by a machine, tangibly embodying a program of instructions executable by a machine to perform method steps to quantify differences between closely related aligned biopolymer sequences, said method steps comprising:

(a) receiving a signal representing a biopolymer test sequence;

(b) determining the identity of a monomer unit at a position m in the test sequence; and (c) outputting a value of 1 for a local matching probability $x_m$ if the monomer unit at position m in the test sequence matches any members of a basis set of biopolymer sequences at position m, or, outputting a value of between 0 and 1 for a local matching probability $x_m$ if the monomer unit at position m in the test sequence does not match any members of the basis set at position m.

10. The program storage device of claim 9 wherein if the monomer unit at position m in the test sequence does not match any members of the basis set at position m, outputting a value of $x_m$ $$x_m = (1-p)^n$$

where p is a number between 0 and 1 and n is the number of sequences in the basis set at position m.

11. The program storage device of claim 9 further comprising the steps of:
performing steps (b) and (c) at a plurality of positions m in the test sequence thereby determining a plurality of local matching probabilities $x_m$; and
determining a global matching probability for the basis set and the test sequence, $X_G$, by forming a product of the plurality of $x_m$.

12. The program storage device of claim 11 wherein the global matching probability for the basis set and the test sequence, $X_G$, is determined by computing the product $$X_G = \prod_1^M x_m.$$

13. The program storage device of claim 9, wherein the test sequence is a 16S RNA sequence from a microorganism, and the basis set comprises a plurality of 16S RNA sequences derived from a collection of microorganisms.

14. A computer system for determining a similarity score for a test sequence and a basis set of sequences comprising:
an input device for inputting a test sequence and a basis set of sequences such that the test sequence and the basis set of sequences are aligned;
a memory for storing the test sequence and basis set;
a processing unit configured for:
determining the identity of a monomer unit at a position m in the test sequence; and
assigning a value of 1 to a local matching probability $x_m$ if the monomer unit at position m in the test sequence matches any members of the basis set at position m, or, assigning a value of between 0 and 1 to a local matching probability $x_m$ if the monomer unit at position m in the test sequence does not match any members of the basis set at position m; and
an output device for outputting a value of $x_m$.

* * * * *